United States Patent
Ahlers

(10) Patent No.: US 6,299,446 B1
(45) Date of Patent: Oct. 9, 2001

(54) RUBBER DAM HOLDER

(76) Inventor: M. Oliver Ahlers, Gustav-Leo-Str. 4, Hamburg (DE)

(*) Notice: Subject to any disclaimer, the term of this patent is extended or adjusted under 35 U.S.C. 154(b) by 0 days.

(21) Appl. No.: 09/434,651

(22) Filed: Nov. 5, 1999

(51) Int. Cl.$^7$ .................................................. A61C 5/12
(52) U.S. Cl. ................................................................ 433/136
(58) Field of Search .............................. 433/136, 137, 433/138

(56) References Cited

U.S. PATENT DOCUMENTS

| | | |
|---|---|---|
| 3,406,452 | 10/1968 | McConville . |
| 3,781,994 | 1/1974 | Hesselgren . |
| 4,204,329 * | 5/1980 | Kahn ..................................... 433/136 |
| 4,544,357 * | 10/1985 | Williams .............................. 433/136 |
| 4,583,946 | 4/1986 | Shanel . |
| 4,600,387 * | 7/1986 | Ross ..................................... 433/136 |
| 4,721,465 * | 1/1988 | Barasz ................................. 433/137 |
| 4,820,155 * | 4/1989 | Sauveur .............................. 433/136 |
| 5,931,673 * | 8/1999 | Bolbolan ............................. 433/136 |

FOREIGN PATENT DOCUMENTS

| | | |
|---|---|---|
| 273 811 | 5/1951 | (CH) . |
| 196 32 084 C1 | 2/1998 | (DE) . |
| 0137090 | 10/1983 | (EP) . |
| 0 178 238 A1 | 4/1986 | (EP) . |
| WO 96/29952 | 10/1996 | (WO) . |

* cited by examiner

Primary Examiner—Ralph A. Lewis
(74) Attorney, Agent, or Firm—Merchant & Gould P.C.

(57) ABSTRACT

A holder for a rubber sheet dam comprises a first frame element. The first frame element includes a cross-member, a first leg has one end connected to the cross-member and a second free end, and a second leg having one end connected to the cross-member and a second free end. A second frame element is substantially congruent to the first frame member, and includes a cross-member, a first leg having one end connected to the cross-member and a second free end, and a second leg having one end connected to the cross-member and a second free end. A first hinge connects the free ends of the first legs, and a second hinge connects the free ends of the second legs. The holder has open and closed states.

4 Claims, 2 Drawing Sheets

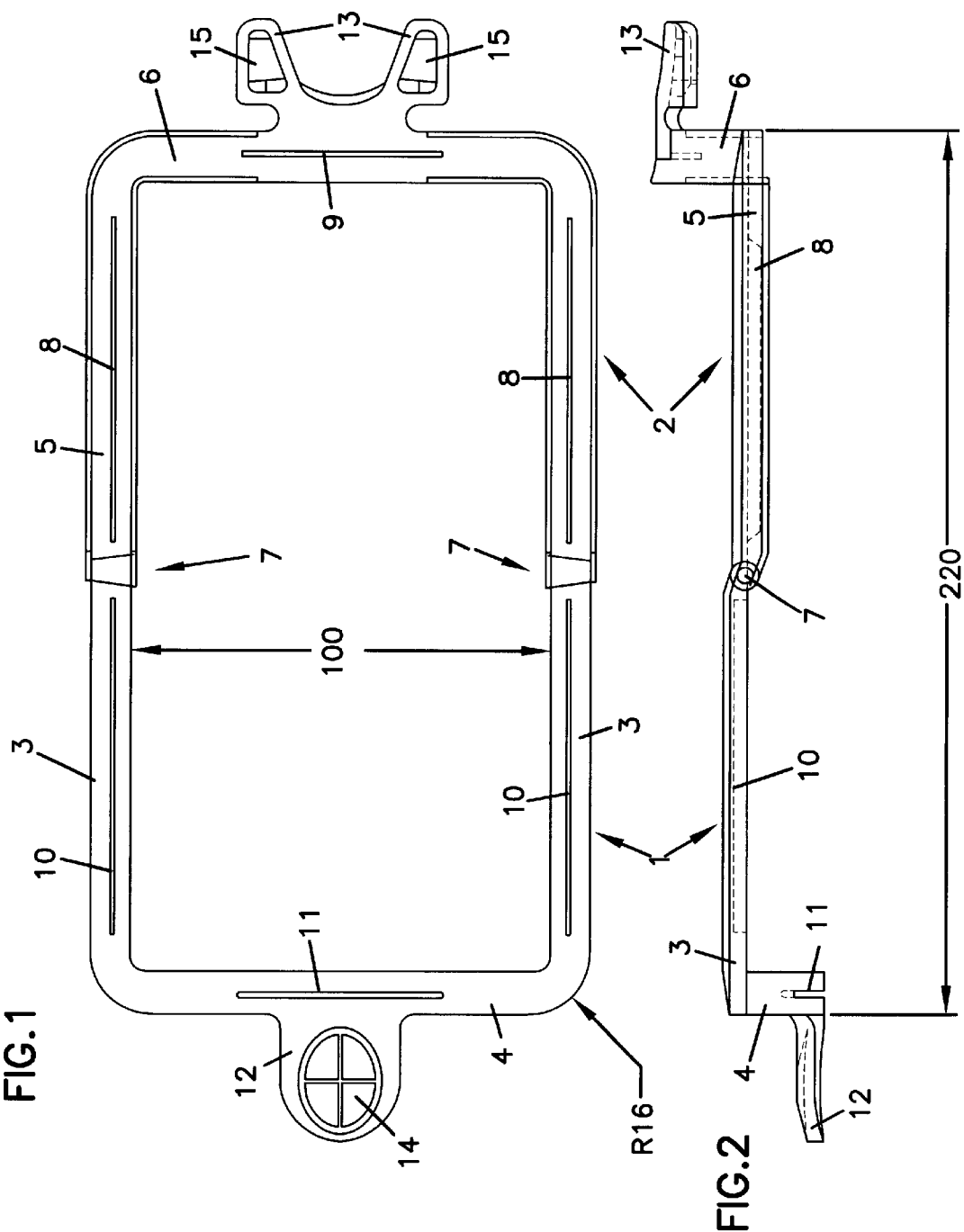

RUBBER DAM HOLDER

TECHNICAL FIELD

The invention comprises a frame-like holder for a rubber barrier sheet designated as a cofferdam or rubber dam.

BACKGROUND

During dental treatment, it is frequently desirable or necessary to isolate and shield the tooth or teeth being treated from the neighboring teeth or the oral cavity in general, for instance in order to prevent saliva from contacting the treated tooth or, inversely, to prevent therapeutic fluids and other agents from contacting the area around the treated tooth. This isolating function is realized by means of a rubber barrier sheet designated as a rubber dam and featuring openings that facilitate extending it over the tooth to be treated or other teeth as well. The sheet isolates and shields the teeth tightly, so as to prevent the passage of liquids.

The rubber sheet surrounding the tooth or teeth in this way is fastened to a retaining device that holds it stretched over the oral opening, allowing access only to the tooth or teeth being treated or other teeth as well, so as to realize its function as described.

The devices now familiar for this purpose are either closed full frames or open (U-shaped) frames made of metal or plastic, over which the rubber sheet is laid, which frames feature pointed projections on which the rubber sheet is suspended and thus retained.

This method of retention of the rubber dam, i.e. of anchoring it to the holder, represents a significant problem in rubber dam applications as per the current state of the art. If the rubber dam comes loose from the holder during dental treatment, its protective shielding effect may be lost in the sense that substances on the outer surface of the rubber dam may enter the oral cavity or that substances from the oral cavity may contaminate the tooth or teeth being treated. This occurs in particular during treatment of the rear molars. In this case, fastening down the rubber dam around the teeth to be isolated, for instance using metal clamps, may be a stubborn problem due to tooth forms that are hardly retentive. In such cases, the rubber dam must not be stretched across the holder so as to form a smooth, taut surface (cf. Winkler "Kofferdam in Theorie und Praxis", Quintessenz Verlags-GmbH 1991), but must rather hang loosely in the frame to some extent. Fulfilling this requirement, however, means the tension required for secure anchoring of the rubber dam to the pointed projections on the frame is lost, greatly increasing the risk of accidental slippage of the rubber dam from the holder.

The purpose of the invention is therefore to provide a frame-like rubber dam holder that is free of the above-described drawback of the current state of the art, thus in particular ensuring secure retention of the rubber dam in all dental treatment situations.

SUMMARY

The invention fulfils this purpose with a holder comprising two practically congruent frame elements, between which the rubber dam can be anchored by means of friction and/or form fit. In this way, the rubber dam is anchored securely to the holder by the elements and action of the holder itself and without requiring tension in the rubber dam, even when a treatment dictates that the rubber dam hang loosely between the legs of the frame.

It is preferable to attach the rubber dam to the holder by having the two frame elements feature interlocking ribs and grooves—the walls of which are placed at appropriate intervals—that deflect the rubber dam and clamp it between the two frame elements. This method of anchoring the dam is independent of any tension in the rubber dam.

It is preferable to design the two frame elements to make a (U-shaped) semi-frame joined by hinged joints at the free ends of the legs of the components. This renders the device easier to work with and facilitates leaving the upper edge of the rubber dam frameless (as is the case in conventional single-element semi-frame holders).

If the ribs and grooves serving to anchor the rubber dam do not exclude the possibility of a lateral shifting of the two frame elements in relation to one another, such a shift during use can be avoided by the additional feature that one of the two frame elements of the holder extend beyond the other when the two frame components are closed.

The known Sauveur frame holder, named after its inventor, is a rubber dam holder comprising two semi-frame elements joined at the free ends of the legs by hinge joints. When hinged open—and not as per the invention when closed—these elements form the rubber dam holder in the form of a closed full frame and the rubber dam is stretched over the surface enclosed by the two semi-frame elements. The hinge axis Is upright In use—and not as per the Invention horizontal—the purpose being to swing away one-half of the rubber darn during treatment to facilitate andodontic x-ray checks. The Sauveur frame retains the rubber dam in as per the currant state of the art by means of the projections on the two semi-frame elements, which projections dig into the rubber dam if the latter is under sufficient tension.

DESCRIPTION OF THE DRAWING

The drawing illustrates the invention in exemplary use; the figures show details as follows:

FIG. 1 Top view of the rubber dam holder as per the Invention with the elements hinged open;

FIG. 2 Laterel view of the holder in FIG. 1;

FIG. 3 Frontal view of the holder in FIG. 1; and

DETAILED DESCRIPTION

Figure 4:
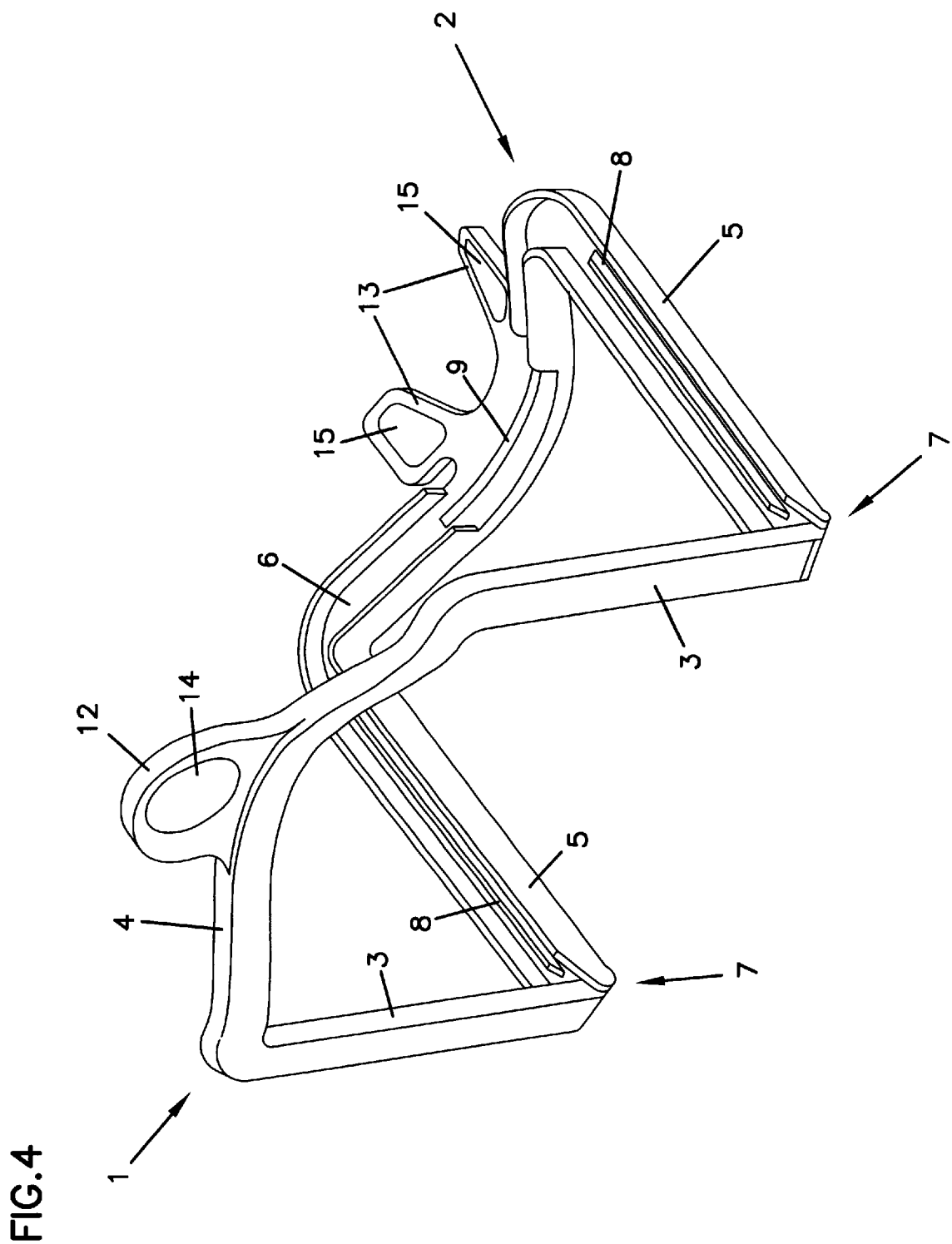
FIG. 4 A perspective view of the holder with the elements hinged half closed.

The rubber dam holder as per the invention comprises mainly two essentially congruent semi-frame elements 1, 2. Semi-frame element 1 comprises two legs 3 and a cross-member 4 connecting them at the end, semi-frame element 2 comprises in the same way two legs 5 and a connecting cross-member 6. At the free ends of legs 3, 5, they are joined in a hinge joint by hinge pins 7 (not shown).

Aside from the ribs and grooves, which will be considered below, semi-frame element 1 features an essentially flat-rectangular cross-section, whereas semi-frame element 2 has a U-shaped cross-section with an internal width such that when the rubber dam holder is closed, element 2 extends somewhat beyond element 1 along both legs 3 and, for the most part, also along the cross-member 4 so as to form in this way a form-fit, or positive, connection between the semi-frame elements 1, 2 that prevents any shifting of the elements relative to one another when the holder is closed. This over-extension of one element also serves to anchor the rubber dam (not shown) between the two semi-frame elements 1, 2; the anchoring of the rubber dam is enhanced by ribs 8, 9, which run along the centre of the groove in leg 5 of element 1 and leg 6 of element 2 the cross-sections of which are U-shaped and, when the rubber dam holder is closed, fit into the complementary grooves 10, 11 in the legs 3 and in the cross-member 4 of semi-frame element 1. The interlocking of the semi-frame elements 1, 2 and the ribs 8, 9 and grooves 10, 11 deflects the rubber dam and clamps it securely between the semi-frame elements 1, 2. This makes it possible to give the rubber dam enough slack to hang loose between the semi-frame elements 1, 2, in particular between the hinge joints 7, but also between the legs 3, 5.

As shown clearly by the drawings in the figures, cross-members 4, 6 of the semi-frame elements 1, 2 feature complementary curves so as to adapt better to the patient's facial form. The two components of a snap in closure 12, 13 are to be located in the middle of legs 4 and 6, which closure will retain the two semi-frame elements 1, 2 in their inter-locked position when the rubber dam holder is in the closed position.

Recesses 14, 15 on components 12, 13 provide the fingers with points of resistance, in particular to aid in opening the holder after use.

What is claimed is:

1. A holder for a rubber sheet dam, the holder comprising:
   a first unitary frame element, the first frame element including a cross-member, a first leg having one end connected to the cross-member and a second free end, and a second leg having one end connected to the cross-member and a second free end;
   a second unitary frame element substantially congruent to the first frame member, the second frame element including a cross-member, a first leg having one end connected to the cross-member and a second free end, and a second leg having one end connected to the cross-member and a second free end; and
   first and second hinges, the first hinge including a pin rotatably connecting the free ends of the first legs and the second hinge including a pin rotatably connecting the free ends of the second legs, wherein the holder has open and closed states, and the first and second unitary frame elements are adapted to hold a rubber sheet there between when the holder is in the closed state.

2. The holder of claim 1 wherein the first frame element overlaps the second frame element when the holder is in the closed state.

3. The holder of claim 1 wherein the first frame element defines a rib and the second frame element defines a groove, wherein the rib mates with the groove and clamps the rubber dam.

4. The holder of claim 3 wherein the first frame element overlaps the second frame element when the holder is in the closed state.

* * * * *